United States Patent
Chlysta

(10) Patent No.: US 11,712,242 B2
(45) Date of Patent: Aug. 1, 2023

(54) SURGICAL PORT CLOSURE DEVICE

(71) Applicant: Walter J. Chlysta M.D., Inc., Cuyahoga Falls, OH (US)

(72) Inventor: Walter J. Chlysta, Massillon, OH (US)

(*) Notice: Subject to any disclaimer, the term of this patent is extended or adjusted under 35 U.S.C. 154(b) by 399 days.

(21) Appl. No.: 17/009,969

(22) Filed: Sep. 2, 2020

(65) Prior Publication Data

US 2020/0397429 A1 Dec. 24, 2020

Related U.S. Application Data

(60) Continuation of application No. 16/185,985, filed on Nov. 9, 2018, now Pat. No. 10,799,236, which is a division of application No. 14/991,163, filed on Jan. 8, 2016, now Pat. No. 10,154,839.

(60) Provisional application No. 62/102,814, filed on Jan. 13, 2015.

(51) Int. Cl.
*A61B 17/12* (2006.01)
*A61B 17/062* (2006.01)
*A61B 17/00* (2006.01)
*A61B 17/06* (2006.01)

(52) U.S. Cl.
CPC ............ *A61B 17/0625* (2013.01); *A61B 2017/00637* (2013.01); *A61B 2017/00663* (2013.01); *A61B 2017/00738* (2013.01); *A61B 2017/0609* (2013.01); *A61B 2017/06047* (2013.01)

(58) Field of Classification Search
CPC ......... A61B 17/00; A61B 17/04; A61B 17/06; A61B 17/12; A61B 17/062; A61B 17/0469; A61B 17/0482; A61B 17/0625; A61B 2017/0063; A61B 2017/0472; A61B 2017/00637
See application file for complete search history.

(56) References Cited

U.S. PATENT DOCUMENTS

| | | | |
|---|---|---|---|
| 5,269,772 A * | 12/1993 | Wilk | A61B 1/00135 604/284 |
| 5,690,652 A | 11/1997 | Wurster et al. | |
| 5,797,927 A * | 8/1998 | Yoon | A61B 17/0469 606/139 |
| 5,860,992 A | 1/1999 | Danie et al. | |
| 5,876,412 A | 3/1999 | Piraka | |
| 8,506,581 B2 | 8/2013 | Wingardner, III et al. | |
| 8,514,054 B2 | 8/2013 | Shah | |
| 8,568,427 B2 | 10/2013 | Nobles et al. | |
| 2012/0016383 A1 * | 1/2012 | Sauer | A61B 17/0483 606/144 |

FOREIGN PATENT DOCUMENTS

| | | |
|---|---|---|
| DE | 19731311 | 1/1999 |
| DE | 19851503 | 5/2000 |
| FR | 2948273 | 1/2011 |

* cited by examiner

*Primary Examiner* — Vi X Nguyen
(74) *Attorney, Agent, or Firm* — Sand, Sebolt & Wernow Co., LPA

(57) ABSTRACT

A port closure device includes a pair of jaws that may move repeatably between open and closed positions and repeatably pass a needle therebetween. The jaws are generally perpendicular to a longitudinal axis of the device in the closed position and generally parallel to the longitudinal axis in the open position. The device further includes a jaw control rod for controlling movement of the jaws and a needle control rod for controlling the passing of the needle between the two jaws.

13 Claims, 9 Drawing Sheets

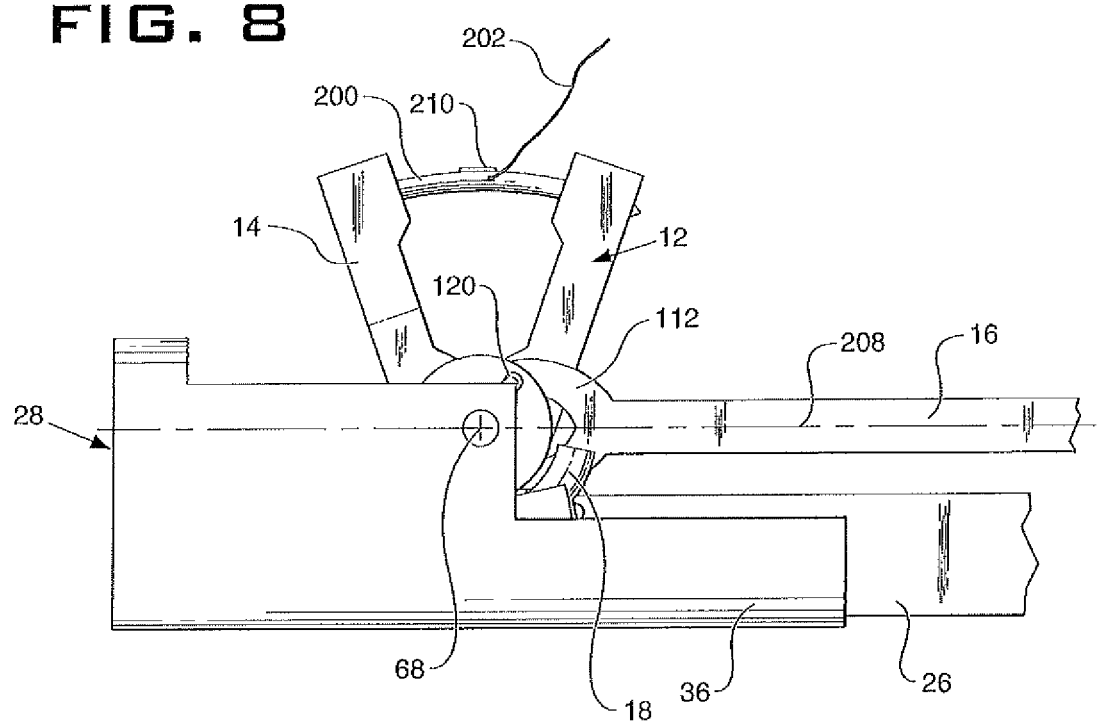
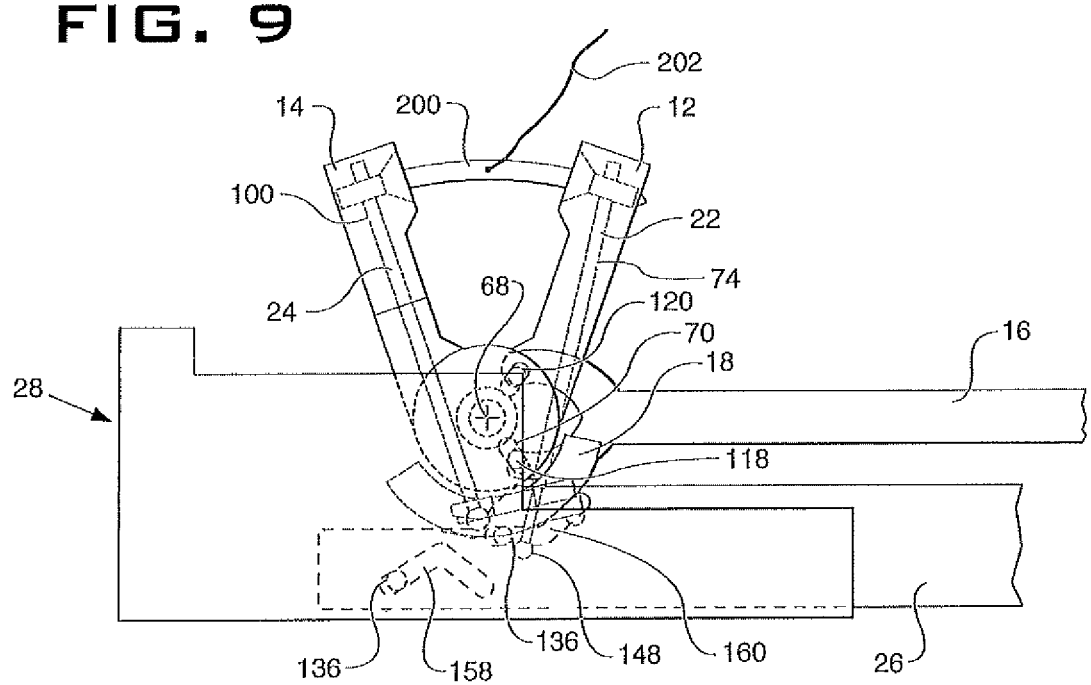

SURGICAL PORT CLOSURE DEVICE

CROSS REFERENCE TO RELATED APPLICATIONS

This application is a Continuation Application of U.S. application Ser. No. 16/185,985 filed on Nov. 9, 2018, which is a Divisional Application of U.S. application Ser. No. 14/991,163, now U.S. Pat. No. 10,154,839, filed Jan. 8, 2016, which claims the benefit of U.S. Provisional Application Ser. No. 62/102,814, filed on Jan. 13, 2015. Each of the above applications and disclosures are incorporated herein by reference as if fully re-written.

TECHNICAL FIELD

The present disclosure relates generally to the field of medical device used during a surgery. More particularly, the present disclosure relates to a suturing device to close ports made during surgery. Specifically, the present disclosure relates to a port closure suturing device that closes a laparoscopic port via suturing jaws carrying a needle and suture, wherein the jaws close in a manner approaching perpendicular relative to the longitudinal axis of the device when the device is oriented vertically

BACKGROUND

Background Information

Laparoscopic surgery is a minimally invasive medical procedure allowing a surgeon to operate from a remote location through small incisions (usually 0.5-1.5 cm) elsewhere in the body. The small incisions are sometimes known as "ports." The surgeon may then insert an endoscope to look inside the body while performing a surgical operation. After the surgical operation, the surgeon must close the ports to prevent further injury at the port site, such as a hernia. One way to close the ports is through the use of one or more sutures. A surgical suture (e.g., stitches) is a medical device that holds body tissues together after an injury or surgical incision.

There have been attempts in the prior art to provide suturing devices for suturing in the abdomen. One such example is U.S. Pat. No. 5,690,652 (the '652 patent) to Wurster et al. which discloses a surgical suturing device especially for endoscopic surgery. Commercially, the '652 patent covers a device known as the "Auto Suture Endo Stitch" offered for sale by Covidien Ltd., of Dublin, Ireland. The '652 patent provides an operating mechanism including a drive and a locking mechanism operated by a handle. Further, the '652 patent includes a suturing head comprising two jaws between which a needle having opposite needle tips and a central eye is exchanged while being alternately locked with the two jaws, wherein the whole procedure being controllable by a single handle. The needle in the '652 patent has a single central aperture receiving the suture string and two slits formed in opposite ends of the needle. The slits are not completely bound, but rather have a general U-shaped cross section.

The movable jaws in the '652 patent are supported on a shaft including a shaft tube. The jaws are operated by means of operating rods which are linked to the jaws at joints. The operating rods are combined further in the back and are actuated together by a push rod. Both jaws are identical and have a longitudinally extending bore receiving the locking pin. When the handle is released, cams remain in place. When the jaws are opened, a thick end portion of the pins slide along the respective front end faces of slide members which are shaped so that the pins remain in position relative to the respective jaws. This allows the needle to remain locked in the needle guide in which it is engaged at that point so that it cannot fall out. The '652 patent further discloses an articulated joint allowing the jaws to pivot such that they are generally perpendicular to the longitudinal axis of the endoscopic stitching device. While the '652 patent appears to have a shaft that can be curved or bent to approximate a perpendicular angle relative to the shaft, it is a large curve and takes up a significant amount of space. This bend length is greater than the diameter of most incision ports. Because of this it appears to be impossible to close a small laparoscopic incision with the device disclosed in the '652 patent.

SUMMARY

Issues continue to exist with suturing devices associated with endoscopic surgeries. Namely, the angles in which the jaws on previous devices close causes difficulty for the surgeon. Further, any articulated joints near the distal end of suturing devices requires the device to be too large to fit within a small port through which an advanced endoscopic camera is inserted. The present disclosure addresses these and other issues.

In one aspect, an embodiment of the disclosure may provide a port closure device comprising: an elongate shaft member extending along a longitudinal first axis defining a lumen therethrough; and first and second jaws carried by the shaft and moveable between an open and a closed position, the jaws rotate about a transverse second axis to move between the open and closed positions; wherein the jaws are generally perpendicular relative to the longitudinal first axis in the closed position. The port closure device may further comprise a needle including an outer surface offset a distance from the longitudinal first axis and generally parallel with the longitudinal first axis when the jaws are in the closed position. Additionally, the port closure device may comprise a pair of control hubs adjacent the first and second jaws; a needle control rod operatively coupled with the hubs and selectively operable by a user; and first and second needle control blades extending through the first and second jaws respectively, a rear end on each control blade coupled with one hub, and the blades adapted to releasably secure a needle to one of the jaws as selected by the user. The port closure device may comprise a jaw control rod including a Y-shaped member including first and second legs; the first leg coupled to the first jaw on one side of the transverse second axis; and the second leg coupled to the second jaw on the other side of the transverse second axis.

In another aspect, the disclosure may provide a method of suturing a surgical port, tissue defect, or fascial defect, the method comprising the steps of: providing a port closure device including first and second jaws carried by a longitudinal shaft and moveable between an open and a closed position; position an outer surface of a needle generally perpendicular a longitudinal axis of the shaft; closing the jaws to pass the needle through live tissue near a port formed in the live tissue, wherein when the needle outer surface is generally parallel with the longitudinal axis when closed within the jaws; transferring the needle from one jaw to the other; and rotating the device 180° about the longitudinal axis and closing the jaws to pass the needle through live tissue near the port's other side.

In another aspect, the disclosure may provide a port closure device including a pair of jaws that may move repeatably between open and closed positions and repeatably pass a needle therebetween. The jaws are generally perpendicular to a longitudinal axis of the device in the closed position and generally parallel to the longitudinal axis in the open position. The device further includes a jaw control rod for controlling movement of the jaws and a needle control rod for controlling the passing of the needle between the two jaws.

In yet another aspect, an embodiment of the disclosure may provide a port closure device comprising: an elongated shaft having a proximal end and a distal end, the shaft extending along a longitudinal first axis defining a lumen therethrough; and first and second jaws carried by the shaft and positioned adjacent the distal end, the first and second jaws moveable between an open and a closed position; a transverse second axis, wherein the first and second jaws rotate about the transverse second axis between the open and closed positions; wherein at least one of the first and second jaws is generally perpendicular to the longitudinal first axis in the closed position; and a needle having opposed first and second sharpened ends configured to pierce live tissue; wherein the needle is selectively transferable between engagement with the first and second jaws and the needle carries a suture string therewith as the needle is transferred, and wherein the needle contacts both the first and second jaws in the closed position and contacts only one of the first and second jaws in the open position.

In another aspect, an embodiment of the disclosure may provide a method of suturing a surgical port comprising the steps of: providing a port closure device including first and second jaws carried by a longitudinal shaft and moveable between an open and a closed position; moving the first and second jaws to the open position, wherein a needle is selectively attached to the first jaw thereby positioning a mid-portion of the needle generally perpendicular to a longitudinal axis of the shaft; moving the jaws to the closed position to pass the needle through live tissue near a port formed in the live tissue, wherein the mid-portion of the needle is generally offset and parallel with the longitudinal axis when closed within the jaws; transferring the needle from the first jaw to the second jaw; moving the jaws to the open position with the needle selectively attached to the second jaw; and rotating the device about the longitudinal axis and closing the jaws to pass the needle through live tissue near the port's other side. In this exemplary summary method, the step of transferring the needle from the first jaw to the second jaw comprises the steps of: removing a first needle control blade disposed within the first jaw from a fully inserted engagement through a completely bound first aperture formed near a first sharpened end of the needle; and inserting a second needle control blade disposed within the second jaw through a completely bound second aperture formed near a second sharpened end of the needle. Additionally in this exemplary summary method, the steps of removing the first needle control blade and inserting the second control blade is accomplished by actuating a needle control switch operatively coupled to a needle control rod extending along the longitudinal axis. Further in this exemplary method, the step of moving the jaws to the closed position further comprises the steps of: passing a sharpened end of the needle along a tapered surface on the second jaw and into a needle cavity defined in the second jaw orthogonal to a needle control bore; wherein the tapered surface guides the needle into the cavity in the event the needle is bent while passing through the live tissue.

In another aspect, an exemplary embodiment of the disclosure may provide a port closure device comprising: a pair of moveable jaws carried by a tubular housing adjacent a distal end, the housing centered along a longitudinal axis, wherein a portion of one of the jaws from the pair of moveable jaws perpendicularly intersects the longitudinal axis in a closed position; a needle selectively transferable between the pair of moveable jaws and carrying a suture string, the suture sting and the needle adapted to pass through live tissue when the needle is selectively transferred from one jaw to the other; and wherein the needle defines at least three completely bound and distinct apertures. This embodiment, as well as other, may further include a first tapered surface on the needle extending into a first aperture formed in a convex surface adjacent a first sharpened end; and a second tapered surface on the needle extending into a second aperture formed in the convex surface adjacent a second sharpened end.

BRIEF DESCRIPTION OF THE SEVERAL VIEWS OF THE DRAWINGS

A sample embodiment of the disclosure is set forth in the following description, is shown in the drawings and is particularly and distinctly pointed out and set forth in the appended claims. The accompanying drawings, which are fully incorporated herein and constitute a part of the specification, illustrate various examples, methods, and other example embodiments of various aspects of the disclosure. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 8 is a side view of the distal end of the port closure device;

FIG. 9 is a side view of the distal end of the port closure device with some components internal to the housing depicted in phantom;

Similar numbers refer to similar parts throughout the drawings.

DETAILED DESCRIPTION

Figure 1:
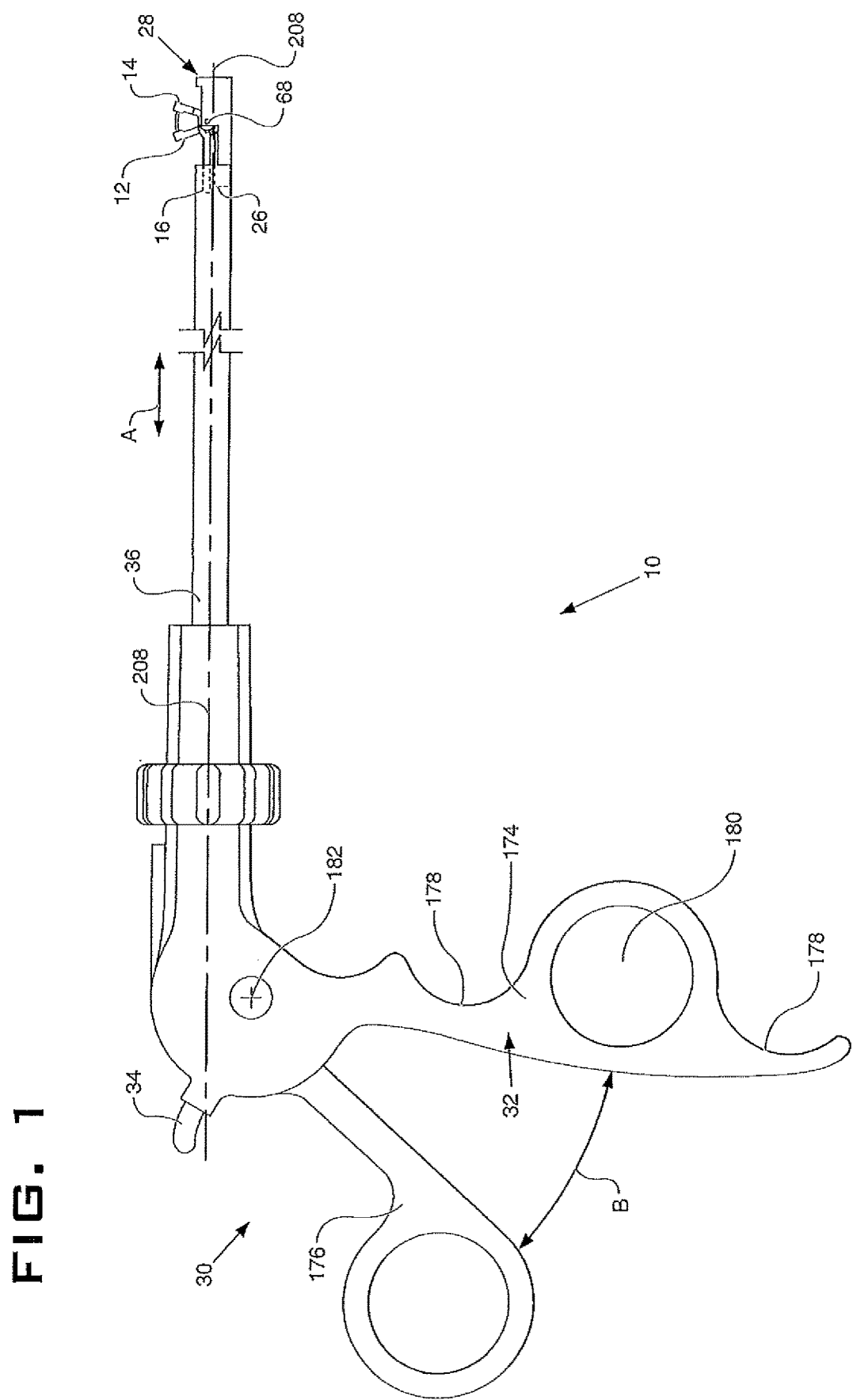
FIG. 1 is a side view of a port closure device of the present disclosure.

A surgical port closure device of the present disclosure is indicated throughout FIGS. 1-10 and generally indicated as 10. Port closure device 10 comprises an upper jaw 12, a lower jaw 14, a jaw pull rod 16, a first hub 18 (FIG. 5), a second hub 20 (FIG. 10), a first needle control blade 22 (FIG. 6), a second needle control blade 24 (FIG. 9), and a needle control rod 26.

As depicted in FIG. 1, port closure device 10 includes a distal end 28 spaced apart from a proximal end 30 defining a longitudinal direction there between. The longitudinal direction is represented by arrow A. A trigger handle assembly 32 is adjacent proximal end 30 and is configured to receive a surgeon's hands therearound for operatively controlling upper and lower jaws 12, 14. A needle moving switch 34 is adjacent handle 32, preferably in a location that may be contacted by the surgeon's thumb. A tubular housing 36 extends from adjacent proximal end 30 towards distal end 28. (The tubular housing 36 may also be referred to herein as an elongated shaft 36). Housing 36 is a tubular member defining a lumen therethrough configured to receive components of the present disclosure operatively coupled with upper and lower jaws 12, 14. Housing 36 is contemplated as being constructed out of a material that is strong and resilient but is also safe for insertion into a human cavity. Housing 36 is not shown to scale in FIG. 1 as indicated by the broken lines. However, it is contemplated that the length of the housing will be approximately 18 inches.

Trigger handle assembly 32 includes a finger receiving member 174 and a thumb receiving member 176. When viewed from the side, finger receiving member 174 is closer to distal end 28 than thumb member 76. Finger member 174 may define a plurality of cutout regions 178 which are configured to receive the surgeon's fingers to allow the surgeon to grip trigger handle 32. Finger receiving member 174 may further define a middle finger aperture 180. Thumb receiving member 176 may define a thumb cutout for receiving surgeon's thumb therethrough. A transverse axis 182 is shown in FIG. 1 by representative cross-hairs indicating that transverse axis 182 extends into and out of the page. The finger receiving member 174 and thumb receiving member 176 are moveable relative to each other in the direction of arrow B about transverse axis 182. This squeezing movement in the direction of arrow B causes operative movement of jaw pull rod 16 within housing 36.

Figure 2:
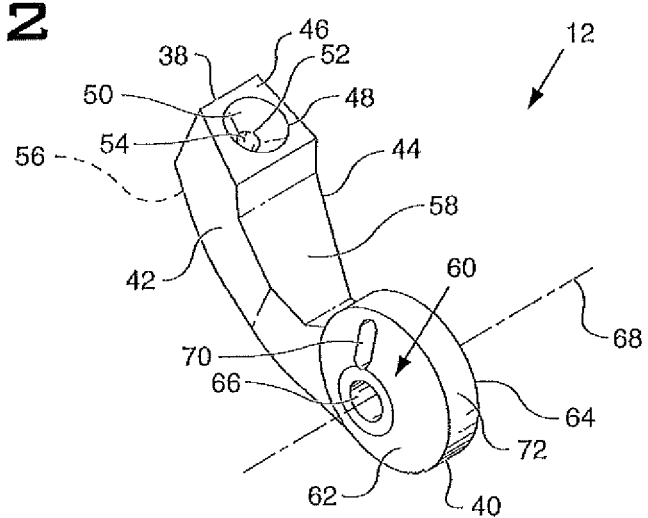
FIG. 2 is a top perspective view of a first jaw for releasably securing a needle thereto as selected by a surgeon.

As depicted in FIG. 2, jaw 12 includes a first end 38 spaced opposite a second end 40. A first sidewall 42 extends from first end 38 towards second end 40. A second sidewall 44 is opposite sidewall 42 extending in the same direction of sidewall 42. A top wall 46 extends between sidewall 42 and sidewall 44 adjacent first end 38. A circular edge 48 defines the top of an opening in top wall 46. A frustoconical sidewall 50 extends downwardly from circular edge 48 to bottom circular edge 52. Frustoconical sidewall 50 is generally a continuous smooth surface between edge 48 and edge 52. Edge 48 has a diameter larger than that of edge 52 such that sidewall 50 tapers inwardly and downwardly when viewed in cross-section. A cylindrical bore 54 extends downwardly from edge 52 towards a bottom wall 56. A top leg wall 58 extends from adjacent top wall 46 towards second end 40. Top leg wall 58 contacts sidewall 42 and sidewall 44 along respective edges extending from first end 38 towards second end 40. An annular member 60 defines second end 40, contacting sidewall 42, sidewall 44, bottom wall 56, and top leg wall 58. Annular member 60 includes a first sidewall 62 facing the same direction as first sidewall 42 and a second sidewall 64 facing the same direction as sidewall 44. Annular member 60 defines a bore 66 extending transversely through upper jaw 12 from sidewall 62 to sidewall 64. Bore 66 is generally cylindrical and circular in cross-section defining a transversely extending rotational axis 68 for jaw 12 to move thereabout. A control aperture 70 is defined by annular member 60 extending from sidewall 62 transversely though member 60 to sidewall 64. Control aperture 70 is eccentric relative to axis 68 and is generally rectangularly shaped with rounded edges when viewed in cross-section. A cylindrical sidewall 72 extends circumferentially around annular member 60, contacting leg wall 58 and sidewalls 42, 44 and bottom wall 56. A bore 74 is defined within jaw 12, extending generally from second end 40 towards first end 38. Bore 74 an has entrance opening formed in sidewall 72 and an end that is adjacent cylindrical bore 54. Bore 74 is in open communication with cylindrical bore 54 adjacent first end 38. Bore 74 is a generally uniform opening that includes a cross-section that is shaped complimentary to that of blade 22.

In one exemplary version of the present disclosure, transverse axis 68 perpendicularly intersects the longitudinal centerline 208 extending through the lumen of housing 36 in a perpendicular manner. Similarly, transverse axis 182 of the trigger handle 32 perpendicularly intersects the imaginary longitudinal center line 208 extending through lumen of housing 36. Accordingly, axis 182 and axis 68 extend along the same transverse plane. However, while this configuration is shown by way of example, clearly other configurations are entirely possible as one having ordinary skill in the art would understand.

Lower jaw 14 is a rigid member constructed of a material similar to that of upper jaw 12. Lower jaw 14 includes a first end 76 spaced apart from a second end 78. An end wall 80 defines first end 76. A first sidewall 82 is spaced opposite a second sidewall 84 and extends from a rigid connection with end wall 80 towards second end 78. A top wall 86 is spaced apart from a bottom wall 88 and extends towards second end from a rigid connection with end wall 80. Annular member 90 defines second end 78 and includes a first sidewall 92, spaced apart and opposite from a second sidewall 94 with a cylindrical sidewall 96 extending therebetween. Annular member 90 defines a cylindrical bore 98 extending through annular 90 from first sidewall 92 to second sidewall 94. Transverse axis 68 extends centrally through bore 96. Jaw 14 includes needle receiving components similar to that of jaw 12, namely a similarly shaped edge 48, a frustoconical sidewall 50, edge 52, and cylindrical bore 54. Jaw 14 further defines a needle control bore 100 (FIG. 9) extending from second end 78 towards first end 76 in a manner similar to that of bore 74 on upper jaw 12. Additionally, a second control aperture 102 is formed and defined in annular member 90 extending from first sidewall 92 to second sidewall 94 eccentric relative to axis 68 of bore 98.

Figure 4:
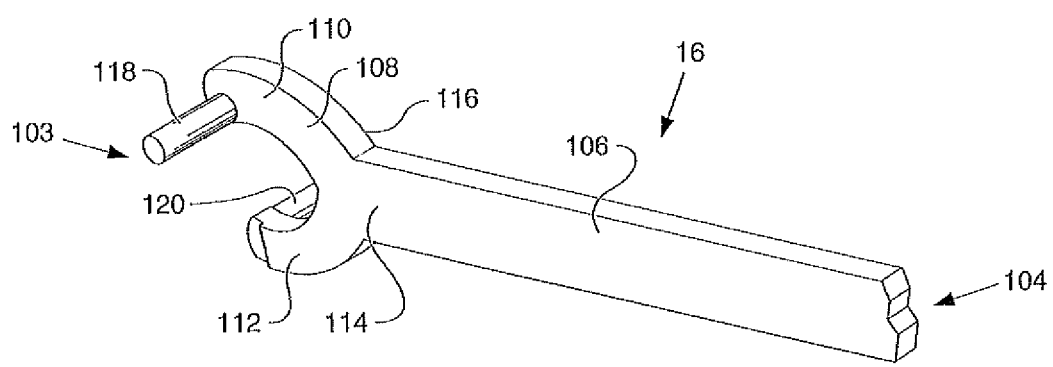
FIG. 4 is a perspective view of a jaw pull rod configured to move the first and second jaws.

As depicted in FIG. 4, jaw pull rod 16 includes a lower end 103 spaced opposite an upper end 104 with an elongated rigid member 106 extending therebetween. Upper end 104 is operatively coupled with trigger handle 32 and positioned within lumen of elongated housing 36. The coupling of upper end 104 to trigger handle 32 may be done in a conventional manner that allows movement of trigger 32 to operatively control movement of jaw pull rod 16. Adjacent the lower end 103 of rigid member 106 is a bifurcating Y-shaped member 108, including a first leg 110 and second leg 112. A first sidewall 114 of jaw pull rod 16 is spaced apart and faces opposite that of a second sidewall 116. A first cylindrical member extends transversely and outwardly from a rigid connection with sidewall 114 on leg 110. A second cylindrical member 120 extends outwardly from sidewall 116 on second leg 112 in a direction opposite that of cylindrical member 118.

Figure 3:
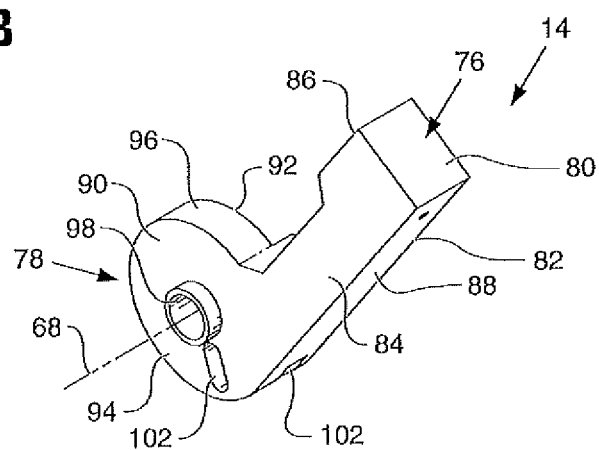
FIG. 3 is a bottom perspective view of a second jaw for releasably securing the needle thereto as selected by the surgeon.

With continued reference to FIG. 2, FIG. 3, and FIG. 4, with device 10 in an assembled position, jaw 12 and jaw 14 are concentric about axis 68 with pull rod 16 sandwiched between jaw 12 and jaw 14. Second sidewall 44 faces the same direction as first sidewall 82 and sidewall 42 faces the same direction as sidewall 84. Downwardly facing top wall 46 faces upwardly facing top wall 86. Y-member 108 on pull rod 16 is positioned between annular member 90 and annular member 60. Cylindrical member 118 extends through first control aperture 70 and cylindrical member 120 extends through second control aperture 102. Cylindrical members 118 and 120 cause relative movement of jaws 12, 14 as pull rod 16 is moved longitudinally in the direction of arrow A towards the proximal end 30 of device 10 by squeezing and movement of trigger mechanism 32. Bore 66 and bore 98 are tandem and concentric next to each other, lined up end to end about axis 68.

Figure 5:
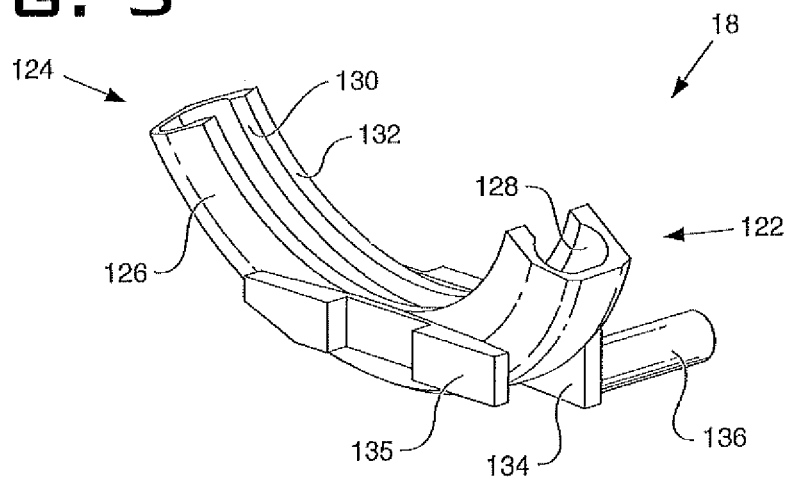
FIG. 5 is a perspective view of a first hub.

As depicted in FIG. 5, first hub 18 is a generally rigid C-shaped member, including a top end 122 and a bottom end 124 with an arcuate wall 126 extending therebetween. While first hub 18 is generally C-shaped when viewed from the side, arcuate wall 126 is a U-shaped member when viewed in transverse cross-section, defining a semi-circular channel 128 therein. First hub 18 may further include an upwardly facing lip 130 closely adjacent a convex top surface 132. The lip 130 may be disposed on each side of channel 128 defining an entrance way into channel 128. The width of the entrance way measured from lip to lip 130 is less than the diameter of channel 128. A support plate 134 is attached to the outer surface of U-shaped wall 126. A second support plate 135 is attached to the opposite side of wall 126. A cylindrical member 136 extends outwardly from support plate 134 generally orthogonal relative to the longitudinal plane defined by channel 128. Cylindrical member 136 is a rigid member formed from a fixed rigid connection with support plate 134 and is configured to move hub 18 as the operator actuates needle control rod 26.

First hub 18 is disposed closely adjacent rear end 40 of annular member 60 and annular member 90 on upper jaw 12 and lower jaw 14, respectively. In one particular embodiment, channel 128 receives annular sidewall 72 therein. Additionally, while second hub 20 is not shown in its own figure, such as FIG. 4 with reference to first hub 18, it is to be understood that second hub 20 is shaped similar to that of first hub 18, except with a cylindrical member that extends in a direction opposite that of cylindrical member 136 on first hub 18.

Figure 6:
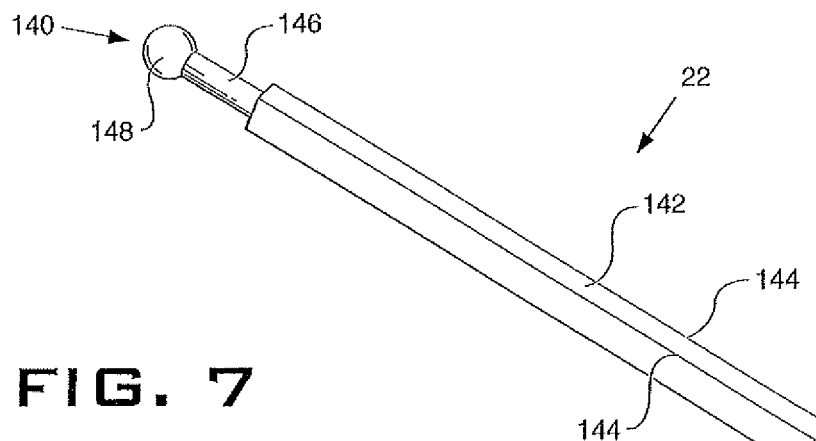
FIG. 6 is a perspective view of a first needle control blade.

As depicted in FIG. 6, first needle control blade 22 includes a forward end 138 spaced apart and longitudinally opposite a rear end 140 with an elongated rigid member body 142 extending therebetween. In the shown embodiment, rigid member body 142 is generally square in cross-section, including longitudinally extending edges 144 connecting planar sidewalls of rigid body 142. Adjacent the rear end of rigid body 142 is a cylindrical throat section 146 that extends from a rigid connection with rigid body 142 towards a ball member 148 that defines rear end 140. In an assembled position, ball member 148 is disposed within channel 128 of first hub 18. Ball 148 has a diameter complimentary to that of channel 128, allowing ball to move freely therein. Ball 148 has a diameter larger than the entranceway between lips 130 such that when ball 148 is slid into channel 128, it cannot be extracted without purposefully moving ball 148 towards the exit adjacent either one of the first end 122 or second end 124. In the assembled position, throat 146 extends through the entranceway defined between lips 130. Additionally, in the assembled position, rigid member 142 extends through bore 74 and is moveable between a retracted position and an advanced position. Second control blade 24 is not shown in an individual view like first blade 22, however it should be understood that second blade 24 is shaped similar to that of first blade 22 and the ball member 148 of second control blade 24 fits within the channel 128 of second hub 20.

Figure 7:
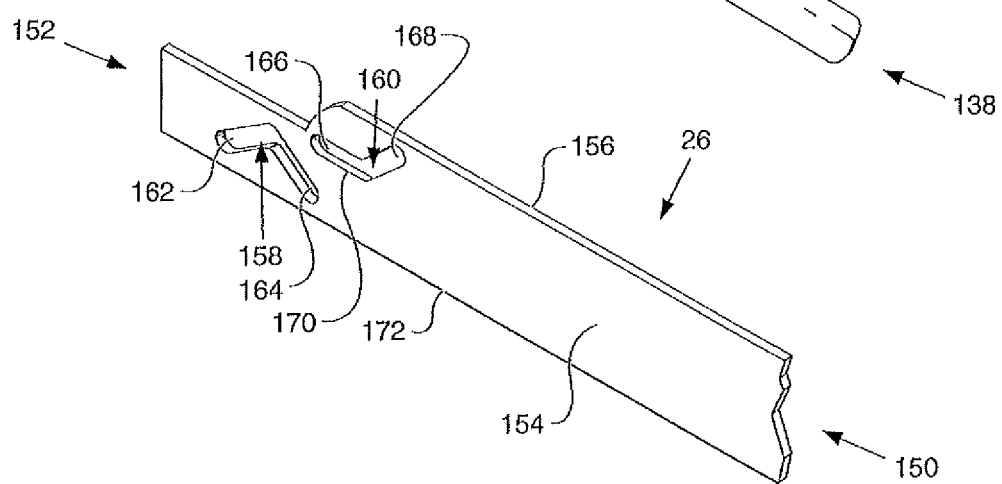
FIG. 7 is a perspective view of a needle control rod.

As depicted in FIG. 7, needle control rod 26 includes an upper end 150 spaced apart and opposite from a lower end 152. Control rod 26 is a planar rigid elongate member with a first sidewall 154 spaced opposite a second sidewall 156. Near lower end 152, rod 26 defines a first slot 158 extending transversely through member 26 from first sidewall 154 to second sidewall 156. A second slot is defined adjacent first slot 158 and also extends from first sidewall 154 transversely through member 26 to second sidewall 156. Second slot 160 is separate and distinct from first slot 158 and generally closer to upper end 150 than first slot 158. First slot 158 is generally an inverted V-shaped member when viewed from the side, including a first leg 162 and second leg 164. The inverted V-shape configuration of slot 158 defines a chevron-like pathway along which cylindrical member 136 travels. Second slot 160 is generally V-shaped when viewed from the side with a first leg 166 and a second leg 168. First leg 166 is partially defined by a bottom edge 170 that is parallel with an edge 172 of rod 26 extending from lower end 152 towards upper end 150. In the assembled state, upper end 150 of rod 26 is operatively coupled with needle movement switch 34. Needle movement switch 34 may actuate rod 26 longitudinally between first and second positions wherein the first position is more advanced than the second position. When port closure device 10 is assembled, cylindrical member 136 on first hub 18 extends through first slot 158 and the cylindrical member on second hub 122 extends through second slot 160. Each respective chevron-like slot 158, 160 defines a path of travel through which cylindrical members 136 of hubs 18, 20 respectively, will travel, as rod 26 linearly moves in a longitudinal direction relative to housing 36 via actuation of switch 34.

In accordance with an aspect of the present disclosure, port closure device 10 provides a pair of jaws that open and close in order to pass a needle back and forth through human tissue in order to close an opening via a suture attached to a needle. When the jaws are in an open position (FIG. 10), the jaws are generally aligned parallel with a longitudinally extending center line. As the jaws are moving from the open position towards a closed position (FIG. 8), the jaws are approaching a transverse plane perpendicular to the longitudinal center line. The jaw closure in this manner allows for the needle to pass through a port in human tissue while the device 10 remains generally vertical relative to the port opening. The vertical alignment of device 10 relative to the port opening makes the passing of the needle through human tissue easier than other conventional prior devices. In accordance with another aspect of the present disclosure, the generally perpendicular jaws in the closed position do not extend far beyond the outer surface of housing 36, which makes the present disclosure desirable for use with small incision ports.

Figure 10:
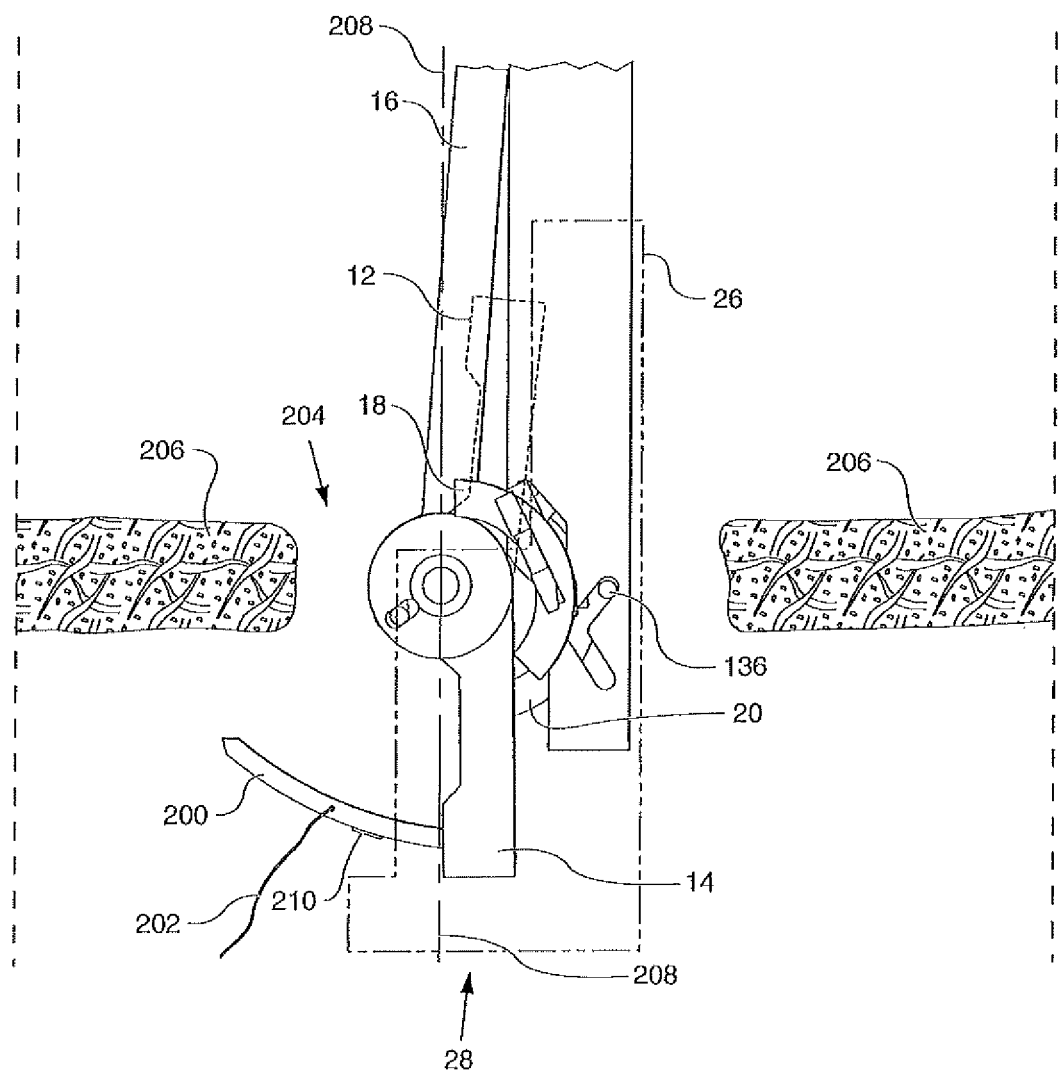
FIG. 10 is an operational side view of the distal end with some internal components depicted in phantom and depicting passing a needle through live tissue.

In operation and with reference to FIG. 8, FIG. 9, and FIG. 10, the assembled device 10 is able to transfer needle 200 carrying suture string 202 between jaws 12, 14 when actuated via switch 34 by a surgeon. The movement of jaws 12, 14 is controlled by rod 16 which is operatively coupled to trigger 32 in a conventionally known manner. The extension of cylindrical member 120 on leg 112 through second control aperture 102 on lower jaw 14 is on one side of the transverse plane defined by rotational axis 68. Here, in FIG. 8, the extension of cylindrical member 120 through second control aperture 102 is shown above rotational axis 68. As can be seen in FIG. 9, cylindrical member 118 extends through aperture 70 on upper jaw 12 below the transversely extending plane defined by rotational axis 68. Stated otherwise, cylindrical members 118, 120 are on different sides of the transversely extending plane defined by rotational axis 68. This alignment moves jaws 12, 14 between an open position and closed position as control rod 16 is moved longitudinally. For example, a surgeon may squeeze trigger 32 in the direction of rotational arrow B (FIG. 1) which imparts longitudinal movement of control rod 16 distally towards second end 28. The distal movement of rod 16 causes cylindrical members 118, 120 to move and impart movement, thus controlling upper jaw 12 and lower jaw 14 respectively. As rod 16 is moved distally toward second end 28, upper jaw 12 is drawn proximally about rotational axis 68 to a position approaching parallel with the longitudinal center line of lumen defined by housing 36. As control rod 16 is moved distally in the direction of distal end 28, cylindrical member 120 rotates lower jaw 14 distally around rotational axis 68 to a position approaching parallel with longitudinal center line of lumen defined by housing 36.

To move upper and lower jaws 12, 14 towards the closed position (FIG. 8), the surgeon moves the trigger handle 32 which imparts a longitudinal movement in the direction of arrow A towards proximal end 30 of control rod 16. The longitudinal movement of control rod 16 in the proximal direction rotates lower jaw 14 about axis 68 in a direction approaching perpendicular to longitudinal axis 208 of housing 36. Similarly, with respect to lower jaw 14, the longitudinal movement of control rod 16 towards the proximal direction rotates lower jaw 14 about axis 68 towards a position approaching perpendicular relative to longitudinal axis 208 of lumen defined by housing 36. The jaws 12, 14 are generally perpendicular relative to the longitudinal first axis 208 in the closed position (FIG. 8).

Needle 200 carrying suture material 202 is transferred between upper jaw 12 and lower jaw 14 selectively by the surgeon. The first blade 22 is disposed within the longitudinal bore 74 of the upper jaw 12 and is moveable between an advanced first position and a retracted second position. Similarly, the second blade 24 is disposed within the longitudinal bore 100 of the lower jaw 14 and is moveable between an advanced first position and a retracted second position. The two blades 22, 24 cannot be in the same position at the same time. Stated otherwise, when the first blade 22 is in the advanced first position, the second blade 24 is in the retracted second position. When the second blade 24 is in the advanced first position, the first blade 22 is in the retracted second position. When either of the blades is in the advanced first position, the edges 144 of rigid member body 142 of the blades contact a notch cutout near the end of needle 200 inside bore 54. The contacting edge 144 with notch cutout of needle 200 releasably attaches needle 200 to that jaw. So, for example, as depicted in FIG. 10, the second blade within lower jaw 14 is in the advanced first position releasably securing needle 200 to lower jaw 14 within bore 54. An outer surface 210 near the center of needle 200 is offset a distance and generally parallel with longitudinal axis 208 when jaws 12, 14 are in the closed position.

The advancement and retraction of first and second blades is controlled by blade and control rod 26. Blade and needle control rod 26 is operatively coupled at its upper end to switch 34. Switch 34 causes longitudinal movement of rod 26 in the direction of arrow A (FIG. 1) when switch 34 is actuated. So, by way of example, when switch 34 is actuated, it moves control rod 26 longitudinally in the distal direction. The cylindrical member on the first hub 18 extends through slot 160 of control rod 26 and cylindrical member 136 of second hub 20 extends through slot 158 on rod 26. Longitudinal movement of control rod 26 causes cylindrical members 136 of first and second hub 18, 20 to move within their respective chevron pathways defined by slots 158, 160. When upper blade 22 is in the retracted second position and lower blade 24 is in the advanced first position, the cylindrical member 136 of hub 18 is in a most distal position within slot 160. In this same position, cylindrical member 136 on hub 20 is in a most distal position extending through slot 158. After the needle 200 has been switched to be releasably secured to upper jaw 12, the blade and needle control rod 26 is actuated in a manner that positions cylindrical members 136 adjacent the proximal end of slots 158, 160 respectively.

In operation and with reference to FIG. 10, port closure device 10 of the present disclosure allows a surgeon to suture a port 204 defined by human tissue 206 in manner that allows the suturing device 10 to remain in a generally vertical position during the suturing process. This is advantageous inasmuch as when a patient is ordinarily operated on, they are lying on an operating table and the plane of port 204 is generally parallel to the ground. Other known suturing devices do not include the aforementioned elements of device 10, requiring a surgeon to attempt to pass a needle through human tissue at an angle that is not vertical which may result in a weak suture which is not beneficial to the patient.

With continued reference to FIG. 10, the distal end 28 of device 10 is passed downwardly through port 204 between two walls of human tissue 206. The jaws 12, 14 are then moved to the open position as depicted in FIG. 10, with the needle releasably secured to the bottom jaw 14. In the open position, the outer surface 210 of needle 200 is perpendicular to longitudinal axis 208. Jaw control rod 16 is moved longitudinally upward towards proximal end by actuating trigger 32 which closes jaw 12 and 14. During the closure of jaws 12, 14, needle 200 passes through human tissue 206, pulling suture 202 therethrough as well. With needle 200 piercing human flesh 206, switch 34 is actuated to release needle 200 from lower jaw 14 and secure needle 200 to upper jaw 12 via blades 22, 24. The jaws are then opened and needle 200 is releasably attached to upper jaw 12 and pulled through human tissue 206 a partial distance such that a portion of suture 202 extends above, below, and through tissue 206. Device 10 is then rotated about its longitudinal axis 208 so that the process may be repeated by passing needle 200 through tissue 206 that defines the other side of port 204. In general, device 10 may be rotated about the longitudinal axis in a range from 45° to 315°, however in one particular embodiment the device is rotated 180°. The other tissue 206 is indicated on the right side of FIG. 10. The surgeon may then tie a surgical knot to suture port 204 closed such that human tissue 206 that defines port 204 is closed and may heal.

Figure 11:
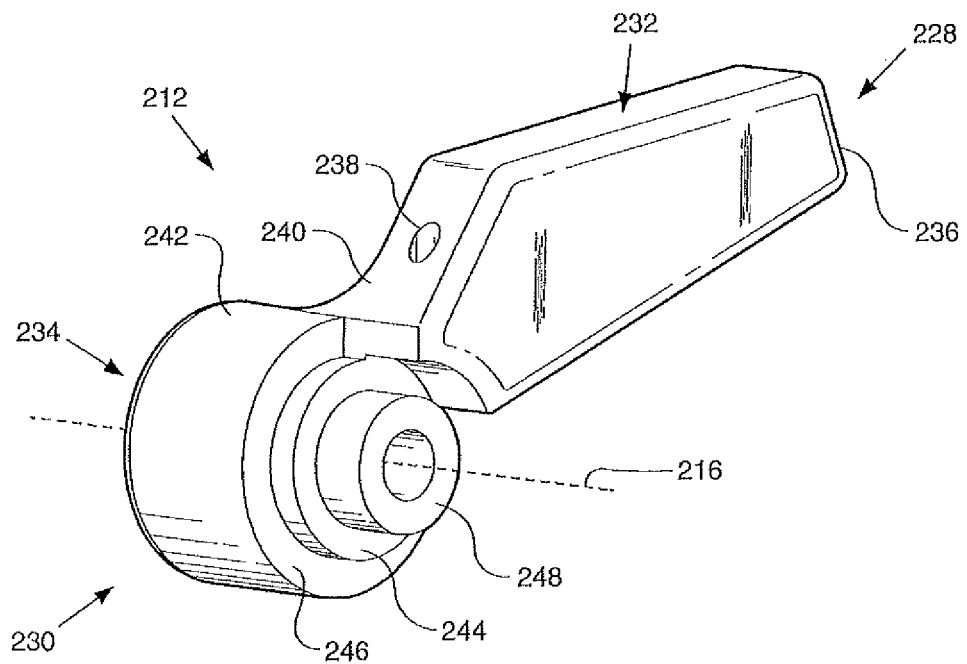
FIG. 11 is a perspective view of an alternative embodiment of an upper first jaw.
Figure 12:
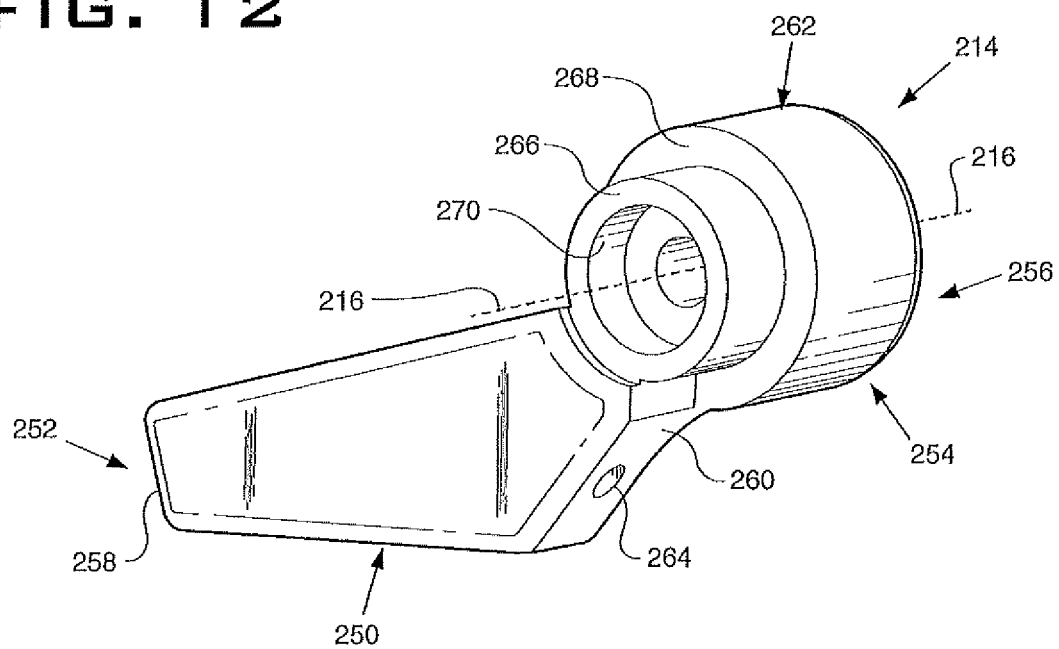
FIG. 12 is a perspective view of an alternative embodiment of a lower second jaw.
Figure 13:
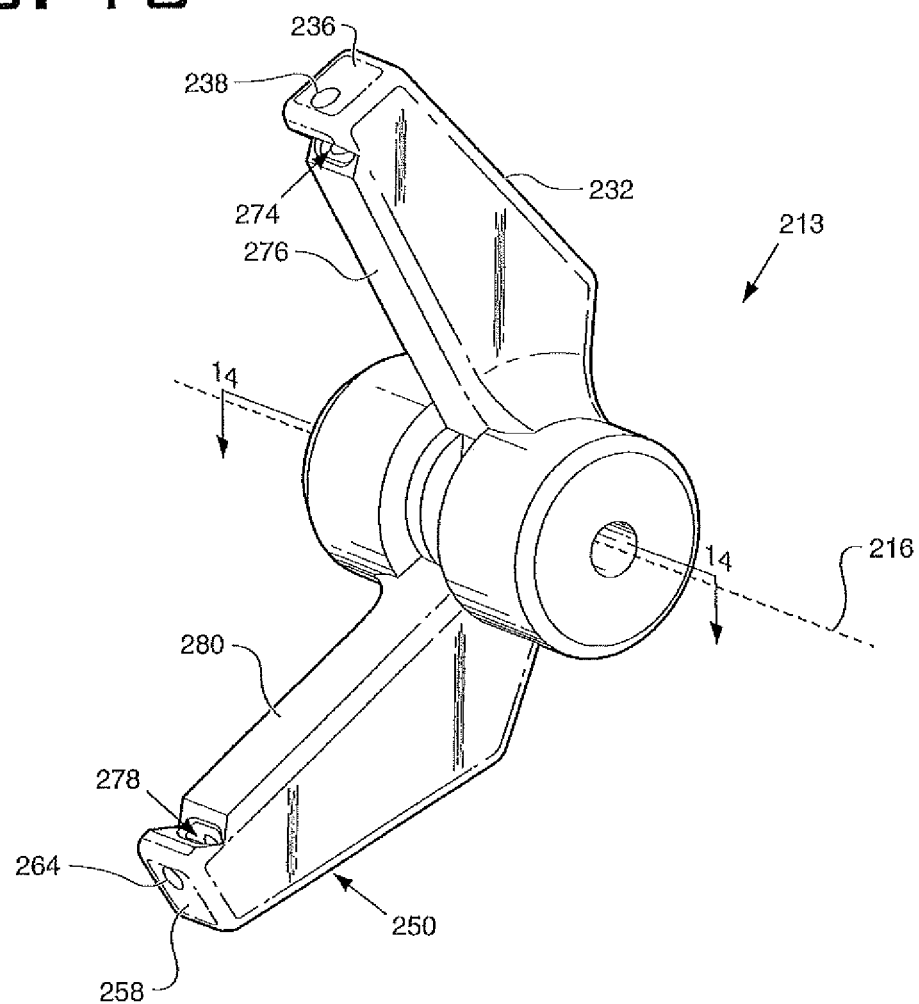
FIG. 13 is a perspective view of an assembled jaw assembly including the alternative embodiment of the first and second jaws.

In accordance with another embodiment of the present disclosure and depicted generally throughout FIG. 11 through FIG. 18, the port closure device 10 may alternatively comprise an upper first jaw 212 and a lower second jaw 214 that form an assembled jaw assembly 213 (FIG. 13). The jaw assembly 213 is carried by the elongated shaft 36 and positioned adjacent the distal end, the first and second jaws 212, 214 moveable between an open and a closed position. Posterior portions of jaw assembly 213 (i.e., posterior refers to being closer to centerline 208 than not) are within the lumen of elongated tubular housing 36 and anterior portions of jaw assembly 213, such as the forward ends of the first and second jaws 212, 214 are exterior the housing 36.

Figure 14:
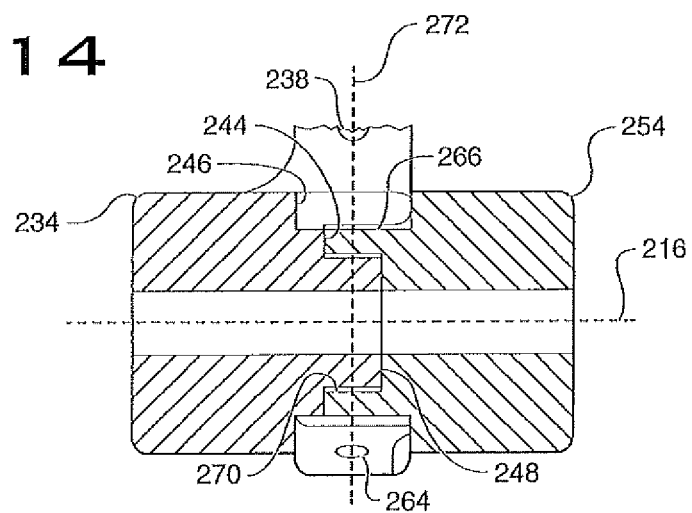
FIG. 14 is a cross section taken along line 14-14 in FIG. 13.

The port closure device 10 embodied in FIG. 11 through FIG. 18 may further comprise a transverse second axis 216, wherein the first jaw 212 and second jaw 214 rotate about the transverse second axis 216 between the open and closed positions. The transverse second axis 216 is perpendicular to and intersects longitudinal centerline 208, which is also commonly referred herein as a longitudinal first axis. The intersection of the longitudinal first axis 208 and the transverse second axis occurs at an imaginary point and is best seen in FIG. 14. At least one of the first and second jaws is generally perpendicular to the longitudinal first axis 208 in the closed position. In one particular embodiment, both the first jaw 212 and the second jaw 214 are generally perpendicular to the elongated tubular housing 36 in the closed position.

As stated above, the transverse axis 216 intersects longitudinal axis 208 at an imaginary intersection. As shown in FIG. 14, the longitudinal axis 208 lies along plane 272. The imaginary intersection is interior the elongated tubular housing 36 and more particularly, interior the assembled jaw assembly 213. This design obviates the need for any additional articulating joints which could move the jaws perpendicular to the direction of longitudinal axis 208.

The port closure device 10 embodied in FIG. 11 through FIG. 18 further comprises a needle 218 having opposed first and second sharpened ends 220, 222 configured to pierce live tissue 206. As will be described in greater detail below, the needle 218 is selectively transferable between engagement with the first jaw 212 and the second jaw 214. Needle 218 carries a suture string (similar to string 202) therewith as the needle 218 is transferred between the two jaws. In the closed position (FIG. 17), the needle 218 contacts both the first and second jaws 212, 214. In the open position, needle 218 contacts only one of the first and second jaws. A mid-portion 224 on needle 218 is offset a distance from the longitudinal first axis 208 and the mid-portion 224 is generally parallel with the longitudinal first axis 208 when the first and second jaws 212, 214 are in the closed position and the mid-portion 224 is generally perpendicular with the longitudinal first axis 208 when the jaws are in the open position. Also, the mid-portion 224 would be offset and generally parallel with the transverse second axis 216 when the jaws 212, 214 are in the open position (FIG. 13). In the open position, the needle 218 contacts only one of the first and second jaws. The needle 218 defines a completely bounded first aperture 227 adjacent the first sharpened end 220 and a completely bounded second aperture 229 adjacent the second sharpened end 222.

As depicted in FIG. 11, first jaw 212 includes a forward end 228 (i.e., anterior) and a rear end 230 (i.e., posterior) which is closer to housing 36 than first end 228 which is farther away from housing 36. First jaw 212 includes an elongated member 232 which defines the first end 228 and an inner/posterior cylindrical member 234 which defines the rear end 230. Elongated member 232 is depicted in FIG. 11 as having a generally rectangular cross section including four walls that extend from a forward/anterior terminal wall 236 towards the rear end 230, however other configurations are entirely possible. The elongated member 232 further defines a needle control bore 238 extending along the length of elongated member 232 from an open communication with forward terminal wall 236 and extending to an open communication with a sloped wall 240. Needle control bore 238 receives a control blade 22 therein. Sloped wall 240 rigidly connects with a cylindrical sidewall 242 on cylindrical member 234. A series of concentric and transversely extending annular members having smaller radii extend outwardly in a transverse direction from an end of cylindrical sidewall 242. As depicted in FIG. 11, an annular member 244 extends transversely outward from an annular end wall 246 and is concentric therewith about transverse axis 216. First annular member 244 has a smaller radius than cylindrical sidewall 242. A second annular member 248 extends transversely in the same direction as first annular member 244 and concentric therewith having a smaller radius creating a stacked configuration of concentric annular members.

As depicted in FIG. 12, lower second jaw 214 includes an elongated member 250 defining a forward end 252 and a cylindrical member 254 defining a rear/posterior end 256. Elongated member 250 includes a forward/anterior terminal wall 258 and a plurality of rigid supporting sidewalls extending towards the second end 256 therefrom. In this shown embodiment, there are four sidewalls having a generally rectangular cross section however, clearly it is entirely contemplated that other structural configurations of the elongated member 250 are entirely possible. Similar to the upper first jaw 212, the lower second jaw 214 includes a sloped wall 260 extending from a portion of the elongated member 250 to a rigid connection with a cylindrical sidewall 262 on cylindrical member 254. A second needle control bore 264 is defined along the length of elongated member 250 in open communication with the forward terminal wall 258 to an open communication with sloped wall 260. Second control bore 264 receives the second control blade 24 therein. Cylindrical member 254 includes at least one annular member 266 extending from a rigid connection with annular end wall 268 and extending transversely therefrom concentric about transverse axis 216. Annular member 266 defines a wall 270 which is configured to receive second annular member 248 on first jaw 212 in an assembled position. Additionally, the width of annular member 266 is equal to that of first annular member 244 and their two radii are the same as well. The respective elongated members of first and second jaws 212, 214 are arranged and rigidly attached to their respective cylindrical members such that when first and second jaws are mated together along the transverse axis 216 that the upper elongated member 232 is generally directly above lower elongated member 250 (see FIG. 14).

More particularly as depicted in FIG. 13 and FIG. 14, in the assembled positions the upper needle control bore 238 is directly vertical above the lower needle control bore 264. This direct vertical alignment is identified in FIG. 14 through the imaginary dashed line 272.

With continued reference to FIG. 13, an upper needle receiving cavity 274 is defined in a longitudinally extending wall 276 on elongated member 232. Needle cavity 274 is adjacent terminal wall 236 and is in open communication with needle control bore 238 as will be described in greater detail below. A second needle cavity 278 is formed in a longitudinally extending wall 280 on elongated member 250 and is in open communication with second needle control bore 264 as will be described in greater detail below.

Figure 15:
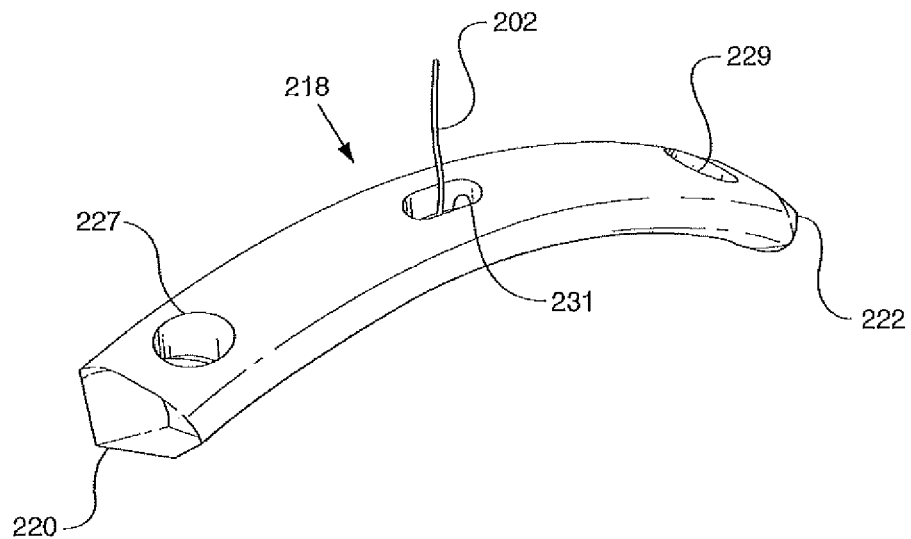
FIG. 15 is an alternative embodiment of a needle having completely bound apertures extending therethrough adjacent first and second ends.
Figure 16:
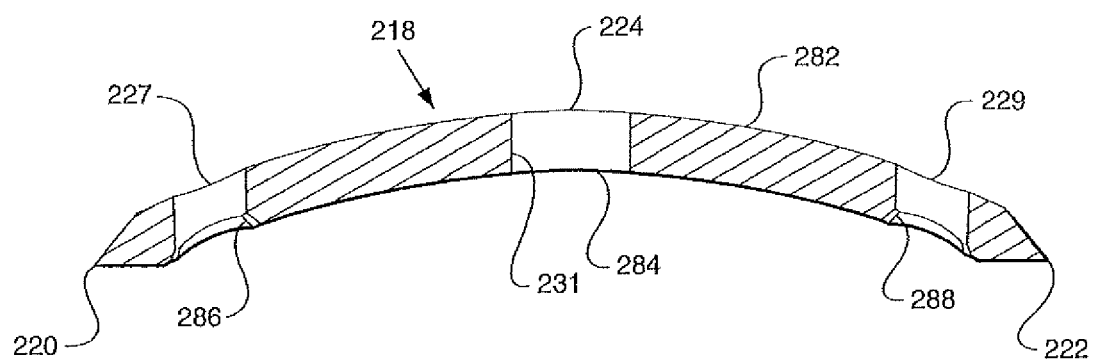
FIG. 16 is a longitudinal cross section of the needle embodiment depicted in FIG. 15.

As depicted in FIG. 15 and FIG. 16, needle 218 has a generally arcuate configuration such that the mid portion 224 is above the sharpened ends 220, 222 when viewed in cross section. When viewed in cross section, needle 218 includes an upwardly facing convex surface 282 and a downwardly facing concave surface 284. The completely bound first aperture 227 adjacent first sharpened end 220 has an inwardly tapering annular surface 286 terminating short (i.e., lower than) of the mid-portion of aperture 227. As depicted in FIG. 16, tapering entrance 286 has a greater diameter at the downwardly facing concave 284 and a narrower diameter along the upper edge of the tapered entrance 286 to form an open communication with aperture 227 extending in a generally cylindrical bore to an open communication but still completely bound within upper surface 282 of needle 218. A second tapered entrance 288 is shaped identical to that of tapered opening 286 however, it is formed in second aperture 229. Apertures 227 and 229 are sized to receive the control blades 22, 24 or control rods therethrough. One exemplary control rod that may be used in association with needle 218 is the control blade 22 identified in FIG. 6 however, other control blades are entirely possible.

Figure 17:
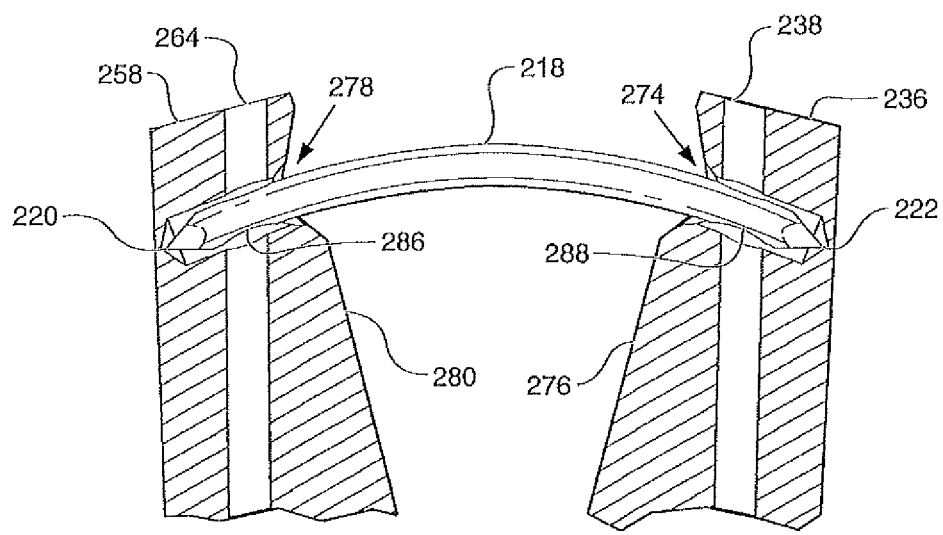
FIG. 17 is a cross section view of the first and second jaws of the alternative embodiment having the needle therein and the first and second jaws in the closed position.
Figure 18:
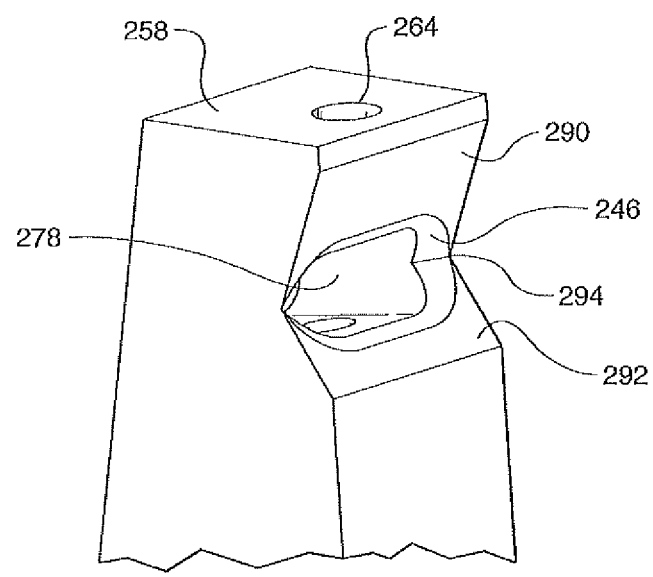
FIG. 18 is a perspective view of an end of the second jaw.

As depicted in FIG. 17 and FIG. 18, the needle cavity 278 and needle cavity 274 are each bound by inwardly tapering walls on their respective legs. As is shown in more detail with respect to FIG. 18, the lower second jaw 212 includes a first tapering wall 290 and a second tapering wall 292. Tapering walls 290, 292 converge towards each other inwardly to a point 294 forming a junction where tapered entrance opening 296 is in open communication with needle cavity 278. It is to be clearly understood that a complementary shaped surface and opening exists on first jaw 212 as depicted in FIG. 17.

In accordance with one non-limiting and exemplary aspect of this embodiment having jaw assembly 213, the present disclosure advances the art of medical devices by providing a suturing device having a jaw perpendicular to the elongated tubular housing/shaft without the need for any articulating joints to alter jaws orientation. In doing so, the present disclosure achieves significant space-savings enabling suturing device 10 to fit within smaller ports than a device requiring articulating joints. This advantage should be readily apparent to one having ordinary skill in the art because the endoscopic cameras used in laparoscopic surgeries are advancing in their own right. As camera technology advances, the physical size of the cameras decrease. Thus, a surgeon only needs to create a small incision/port to fit the advanced camera through. Older prior art suturing devices are simply too large to fit within and properly close the smaller ports that are used in association with the advanced endoscopic cameras.

In operation and with respect to assembled jaw assembly 213, needle 218 is configured to be received in each of the first and second jaws 212, 214 in the closed position as depicted in FIG. 17. In the closed position, first end 220 is fully received within cavity 278 and second end 222 is fully received within cavity 274. First aperture 227 is aligned with needle control bore 264 and second aperture 229 is aligned with needle control bore 238. This allows the transfer of a needle control blade 22, 24 as described above with respect to FIG. 1 through FIG. 10 to selectively extend through either one of aperture 227 or aperture 229 to selectively engage the needle such that it remains selectively attached to one of the jaws in the open position.

To open the jaw assembly 213 from the closed position (FIG. 17), the surgeon will actuate the trigger handle assembly 32 identified in FIG. 1 that operatively controls the upper and lower jaws 212, 214 of assembled jaw assembly 213. Similarly, the needle moving switch 34 is operatively coupled to control blades 22, 24 which are disposed within first bore 238 and second bore 264 to effectuate transfer of needle 218 between first jaw 212 and second jaw 214. Similar to the view identified in FIG. 10, when the surgeon actuates the trigger assembly, jaw assembly 213 moves from its closed position identified in FIG. 17 to an open position similar to that identified in FIG. 10. In this shown state, a control blade extends through completely bounded first aperture 227 on needle 218 securing needle 218 to second jaw 214. When the port closure device 10 is in the open position, the mid-portion 224 of needle 218 is generally perpendicular to longitudinal center line 208. The second end 222 of needle 218 is exposed and disconnected from first jaw 212 allowing the first end to pierce live tissue 206 defining a port 204 as the surgeon actuates the trigger handle assembly 32 to move the jaws from the open position towards the closed position. As the jaws are closing, the sharpened end 222 pierces live tissue passing suture 202 therethrough. With the live tissue 206 pierced and the jaws in a closed position, the surgeon may then actuate the needle moving switch which will transfer the securement of needle 218 from lower jaw 214 to upper jaw 212. This is done by a needle control rod withdrawing from aperture 227 and another needle control rod in upper jaw 212 extending into aperture 229. With the needle selectively attached to upper jaw 212, the surgeon may release the trigger assembly 32 to pull the needle 218 through the pierced live tissue 206 pulling suture 202 therewith. The surgeon may then rotate the port closure device 10 180° to pierce live tissue on the other side of port 204 and suture the other side of the live tissue 206 in a similar manner as that described above.

In some real world instances, live tissue 206 may be difficult to pierce and may require manual physical exertion on behalf of the surgeon. In these instances, it may be possible for some of the components of port closure device 10 to bend slightly such as the needle becoming slightly bent. In order to solve this need, the entrance openings 274 and 278 to their respective jaws have tapered walls 290, 292 meeting at a junction point which act as guide walls in the event that needle 218 becomes slightly bent and the ends 220, 222 need guided assistance into their respective apertures 274, 278.

To further assist the selective securement of needle 218 to jaw 212 or jaw 214 in the open position, the apertures 227 or 229 on needle 218 are fully bound, meaning that it is a complete through aperture and not just a slit along the side edge of the needle, which is the most common form of needle in the general surgical arena to date. The completely bound aperture 227, or 229 ensure that the needle control blades 22, 24 prevent needle 218 from loosening from its selective engagement with either one of jaw 212 or jaw 214 when the jaw assembly 213 is in the open position. This is especially critical during surgical scenarios to ensure the needle 218 is not lost within the patient.

The three completely bound apertures on needle 218 are distinct and separate. Particularly, the outer apertures 227, 229 receive the control blades 22, 24 and a central third completely bound aperture 231 receives suture 202 therethrough.

In the foregoing description, certain terms have been used for brevity, clearness, and understanding. No unnecessary limitations are to be implied therefrom beyond the requirement of the prior art because such terms are used for descriptive purposes and are intended to be broadly construed.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Moreover, the description and illustration of various embodiments of the disclosure are examples and the disclosure is not limited to the exact details shown or described.

What is claimed:

1. A port closure device comprising:
   an elongated housing having a proximal end and a distal end, the elongated housing extending along a longitudinal first axis;
   first and second jaws positioned adjacent the distal end of the elongated housing, the first and second jaws moveable between an open and a closed position;
   a transverse second axis intersecting the longitudinal first axis, wherein at least one of the first and second jaws rotate about the transverse second axis between the open and closed positions;
   wherein both the first and second jaws are not parallel to the longitudinal first axis in the closed position; and
   wherein the port closure device is adapted to carry a needle having opposed first and second sharpened ends configured to pierce live tissue; wherein the port closure device enables the needle to be selectively transferable between engagement with the first and second jaws and the needle adapted to carry a suture string therewith as the needle is transferred, and wherein the first and second jaws are adapted to respectively cover the first and second sharpened ends of the needle in the closed position and only one of the first and second jaws respectively covers the first and second sharpened ends of the needle in the open position.

2. The port closure device of claim 1, wherein the first jaw comprises:
   a wall having an bounded edge defining an opening adapted to receive the needle therethrough in the closed position;
   wherein the opening is offset from the longitudinal first axis in the closed position.

3. The port closure device of claim 1, wherein the first jaw comprises:
   a frustoconical sidewall defining a portion of an opening adapted to receive the needle therein in the closed position;
   wherein the opening is offset from the longitudinal first axis in the closed position.

4. The port closure device of claim 3, wherein the first jaw further comprises:
   a needle control bore formed in the first jaw, wherein the needle control bore is in operable communication with the opening.

5. The port closure device of claim 1, wherein the first jaw comprises:
   an annular member defining a transverse bore coaxial with the transverse second axis.

6. The port closure device of claim 1, further comprising:
   a longitudinally extending cylindrical outer sidewall of the elongated housing;
   a first end on the first jaw, wherein the first end on the first jaw is offset transversely from the cylindrical outer sidewall when the first and second jaws are in the closed position, and the first end on the first jaw is closer to the longitudinal first axis than the cylindrical outer sidewall when the first and second jaws are in the open position.

7. The port closure device of claim 1, wherein the first jaw comprises:
   an anterior end and a posterior end; and
   an elongated member that defines the anterior end and is generally rectangular in cross section.

8. The port closure device of claim 1, wherein the first jaw comprises:
   an anterior end and a posterior end;
   an elongated member that defines the anterior end; wherein the elongated member has a length; and
   wherein the length of the elongated member positions the anterior end farther from the longitudinal axis than the elongated housing when the first and second jaws are in the closed position.

9. The port closure device of claim 8, wherein the first jaw further comprises:
   a terminal wall at the anterior end;
   a needle control bore defined within the elongated member extending along at least a portion of the length of the elongated member; and
   an opening defined in the terminal wall in open communication with the needle control bore.

10. The port closure device of claim 9, further comprising:
    a control blade disposed within the needle control bore.

11. The port closure device of claim 1, wherein the first jaw comprises:
    an anterior end and a posterior end;
    an elongated member that defines the anterior end; and
    an annular member that defines the posterior end, wherein the annular member is centered along the transverse second axis.

12. The port closure device of claim 1, further comprising:
    wherein the first jaw defines a first needle control bore and the second jaw defines a second needle control bore wherein the first and second needle control bores;
    a needle control switch on a handle assembly operatively coupled to a first needle control blade and a second needle control blade; wherein the first needle control blade is disposed with the first needle control bore and the second needle control blade is disposed within the second needle control bore.

13. The port closure device of claim 1, further comprising:
    a mid-portion on the needle offset a distance from the longitudinal first axis and the mid-portion generally parallel with the longitudinal first axis when the jaws are in the closed position and the mid-portion generally perpendicular with the longitudinal first axis when the jaws are in the open position and the needle is contacting only one of the first and second jaws.

* * * * *